United States Patent [19]

Ishino et al.

[11] Patent Number: 5,217,888
[45] Date of Patent: Jun. 8, 1993

[54] YEAST WITH HIGH CONTENT OF ARGININE

[75] Inventors: Shuichi Ishino; Takahiro Hara; Sadao Teshiba, all of Machida, Japan

[73] Assignee: Kyowa Hakko Kogyo Co., Ltd., Tokyo, Japan

[21] Appl. No.: 689,055

[22] PCT Filed: Aug. 27, 1990

[86] PCT No.: PCT/JP90/01080

§ 371 Date: May 2, 1991

§ 102(e) Date: May 2, 1991

[87] PCT Pub. No.: WO91/03546

PCT Pub. Date: Mar. 21, 1991

[30] Foreign Application Priority Data

Sep. 4, 1989 [JP] Japan ................... 1-228848

[51] Int. Cl.$^5$ ................ C12N 15/00; C12N 1/16; C12P 13/10
[52] U.S. Cl. .................... 435/172.1; 435/114; 435/244; 435/245; 435/255; 435/911; 435/173.1
[58] Field of Search ............ 435/255, 911, 244, 114, 435/245, 172.1, 173

[56] References Cited

U.S. PATENT DOCUMENTS

| | | | |
|---|---|---|---|
| 3,801,456 | 4/1974 | Kubota et al. | 435/244 |
| 3,833,473 | 9/1974 | Kubota et al. | 435/244 |
| 3,887,435 | 6/1975 | Nakamura et al. | 435/911 |
| 4,439,525 | 3/1984 | Shay et al. | 435/172.1 |
| 4,463,094 | 7/1984 | Chibata et al. | 435/172.1 |
| 4,582,801 | 4/1986 | Hamada et al. | 435/172.1 |

FOREIGN PATENT DOCUMENTS 2145466 3/1973 Fed. Rep. of Germany .

OTHER PUBLICATIONS

ATCC "Catalogue of Fungi/Yeasts" 17th Edition 1987 Jong et al. Editors pp. 198-200 Rockville, Maryland.
APS JPOABS J59:151894 Hino et al. Aug. 30, 1984.
APS JPOABS J59:55194 Nakamura Mar. 30, 1984.
Eur. J. Biochem. 12 No. 1 (1970), F. Ramos, P. Thuriaux, J. M. Wiame and J. Bechet "The Participation of Ornithine and Citrulline in the Regulation of Arginine Metabolism in *Saccharomyces cerevisiae*" pp. 40-47.
Chemical Abstracts, vol. 98, No. 13, Mar. 28, 1983, Columbus, Ohio, Abstract No. 104060J, Sawnor-Korszynska Danuta et al.; 'Secondary Effects of the Ethionine-resistance mutation in Saccharomycopsis Lipolytica.', p. 332, col. L, & Acta Biochim, Pol. vol. 29, No. 1-2, 1982, pp. 151-157.

Primary Examiner—Herbert J. Lilling
Attorney, Agent, or Firm—Antonelli, Terry, Stout & Kraus

[57] ABSTRACT

The present invention relates to yeast with a high arginine content which belongs to *Kluyveromyces polysporus* and has resistance to ethionine.

7 Claims, No Drawings

YEAST WITH HIGH CONTENT OF ARGININE

TECHNICAL FIELD

The present invention relates to yeast capable of accumulating L-arginine in the cells in large quantities. The yeast cells of the present invention are expected to be utilized as feed for livestock.

BACKGROUND ART

Heretofore yeast cells such as Torula yeast and beer yeast have been utilized as feed for livestock.

However, some livestock cannot be sufficiently supplied with some amino acids from yeast cell source alone. For example, domestic fowls tend to suffer from insufficiency of L-arginine. Insufficient amino acids are supplemented by addition of each amino acid, but this is not economically advantageous. If various kinds of yeasts are provided which are capable of accumulating insufficient amino acids in the cells in large quantities, the yeast cells would be widely utilized as feed for livestock.

As yeast capable of accumulating L-arginine in the cells in large quantities, there is known a regulatory mutant (argR, cpoO) belonging to the genus Saccharomyces which accumulates 1.7% of L-arginine in the cells [Eur. J. Biochem., 12, No. 1, 40-47 (1970)].

DISCLOSURE OF THE INVENTION

According to the present invention, ethionine-resistant strains belonging to the genus Kluyveromyces can be provided as yeast capable of accumulating L-arginine in the cells in large quantities. These strains are yeasts with a high arginine content which contain at least 5% (on a dry cell weight basis) of free L-arginine in the cells.

The yeast with a high arginine content of the present invention includes any yeast which belongs to *Kluyveromyces polysporus* and has resistance to ethionine. Yeast having such properties can be obtained by using yeast belonging to the genus Kluyveromyces as a parent strain, and subjecting the strain to a conventional mutation treatment, for example, UV irradiating or a chemical treatment with N-methyl-N'-nitro-N-nitrosoguanidine, etc. and selecting yeast capable of accumulating at least 5% (on a dry cell weight basis) of L-arginine in the cells from mutants which have acquired resistance to ethionine. Any yeast may be usable as the parent strain so long as it belongs to the genus Kluyveromyces. A specific example is *Kluyveromyces polysporus* IFO 0996 [Int. J. Syst. Bact., 38, 822 (1983)].

The process for obtaining the yeast with a high arginine content of the present invention is described specifically below.

As the parent strain, *Kluyveromyces polysporus* IFO 0996 was used. Cells of the parent strain were suspended in a physiological saline solution to a density of $10^8$ cells/ml. The suspension (0.1 ml) was smeared on a minimum agar medium [20 g/l glucose, 6.7 g/l Yeast Nitrogen Base (manufactured by Difco), 20 g/l agar; pH 5-6] containing 1000 µg/ml ethionine. The plate was put under a UV light source (15 W ultraviolet lamp, wavelength; 253Å) at a distance of 35 cm from the light source and exposed to UV rays for 20 seconds. The agar plate irradiated with UV rays was incubated at 30° C. for 2-4 days. About 250 colonies of ethionine-resistant strains grew on the surface of the ethionine-containing medium. Two hundred ethionine-resistant strains were picked up and cultured in a manner similar to Example 1 described below. Some ten strains which accumulated more than 5.0% of L-arginine in the cells were selected. One of them was named *Kluyveromyces polysporus* ETA82-33 and was deposited with the Fermentation Research Institute, Agency of Industrial Science and Technology, Japan as FERM BP-2560 on Aug. 22, 1989, under the Budapest Treaty.

As the medium for culturing the yeast with a high arginine content of the present invention, there may be used a nutrient medium or a synthetic medium containing carbon sources, nitrogen sources, inorganic salts, growth factors, etc.

As the carbon source, any carbohydrates such as glucose, fructose, sucrose, molasses, starch, starch hydrolyzate and fruit juice, alcohols such as ethanol, methanol and propanol, etc. may be used so long as the yeast can assimilate them.

As the nitrogen source, ammonium sulfate, ammonium nitrate, ammonium chloride, ammonium phosphate, ammonium acetate, urea, ammonia, amines, peptone, meat extract yeast extract, corn steep liquor, casein hydrolyzate, various fermented cells and their digestion products, etc. may be used.

As the inorganic salts, potassium dihydrogen phosphate, dipotassium hydrogen phosphate, magnesium phospate, magnesium sulfate, sodium chloride, ferrous sulfate, manganese sulfate, calcium carbonate, etc. may be used.

When nutrient-requiring mutants are used, preparations of nutrients which are growth factors or natural substances containing the nutrients are added. For example, amino acids such as lysine and glutamic acid, vitamins such as biotin and thiamine, and nucleic acid bases such as purine and adenine are used.

Cultivation is carried out under aerobic conditions, for example, with aeration and agitation, by maintaining the temperature at 24°-37° C. and the pH at 4-9, and is completed generally in 2 to 7 days. The pH is controlled by using urea, calcium carbonate, ammonia gas, aqueous ammonia, magnesium phosphate, ammonium carbonate, or the like. After the completion of cultivation, the cells are harvested from the culture and dried, whereby the yeast with a high arginine content can be obtained. The cells can be harvested and dried by known techniques, e.g., by using a sharples and a spray drier.

BEST MODE FOR CARRYING OUT THE INVENTION

Example 1

*Kluyveromyces polysporus* ETA82-33 as used as the seed strain. ETA 82-33 was inoculated into a test tube containing 5 ml of a seed medium comprising 10 g/l glucose, 5 g/l peptone and 3 g/l yeast extract (pH 6.0), and subjected to shaking culture at 30° C. for 24 hours.

The resulting seed culture (0.05 ml) was inoculated into a test tube containing 6 ml of a cell culture medium [50 g/l glucose, 34 g/l corn steep liquor, 3.8 g/l $(NH_4)_2SO_4$, 1 g/l $MgSO_4 \cdot 7H_2O$, 1 g/l $KH_2PO_4$, 30 g/l $CaCO_3$ (pH 6.5)]. Cultivation was carried out with shaking at 30° C. for 48 hours. After the completion of cultivation, the cells were harvested by centrifugation and washed twice with 67 mM phosphate buffer (pH 6.0). Then, 0.1 g (on a dry cell weight basis) of the yeast cells was suspended in 2 ml of 67 mM phosphate buffer, followed by extraction at 100° C. for 10 minutes. Free L-arginine in the extract was quantitatively determined and it was found that 8.0% of L-arginine was accumulated based on the dry cell weight.

As a control, *Kluyveromyces polysporus* IFO 0996, which is the parent strain, was cultured in the same manner as described above. The amount of L-arginine accumulated was 0.2% based on the dry cell weight.

Example 2

*Kluyveromyces polysporus* ETA82-33 was used as the seed strain. ETA 82-33 was inoculated into a test tube containing 30 ml of a seed medium comprising 10 g/l glucose, 5 g/l peptone and 3 g/l yeast extract (pH 6.0), and subjected to shaking culture at 30° C. for 24 hours.

The whole of the resulting seed culture was inoculated into a 2-l fermenter containing 1000 ml of a cell culture medium [50 g/l glucose, 34 g/l corn steep liquor, 3.8 g/l $(NH_4)_2SO_4$, 1 g/l $MgSO_4.7H_2O$, 1 g/l $KH_2PO_4$, (pH 6.5)]. Cultivation was carried out with stirring at 30° C. for 40 hours, during which the pH was adjusted to 5.5 with aqueous ammonia. After the completion of cultivation, the cells were harvested by centrifugation and washed twice with 67 mM phosphate buffer (pH 6.0). Then, 0.1 g (on a dry cell weight basis) of the yeast cells was suspended in 2 ml of 67 mM phosphate buffer, followed by extraction at 100° C. for 10 minutes. Free L-arginine in the extract was quantitatively determined and it was found that 13.0% of L-arginine was accumulated based on the dry cell weight.

As a control, *Kluyveromyces polysporus* IFO 0996, which is the parent strain, was cultured in the same manner as described above. The amount of L-arginine accumulated was 0.2% based on the dry cell weight.

INDUSTRIAL APPLICABILITY

According to the present invention, there can be provided yeast with a high L-arginine content which is useful as yeast for feed.

We claim:

1. A biologically pure culture of the yeast *Kluyveromyces polysporus* ETA 82-33 (FERM BP-2560).

2. A process for producing a yeast with a high arginine content which comprises subjecting a yeast belonging to the genus Kluyveromyces to a mutation treatment, selecting desired yeast belonging to said genus having ethionine resistance and being capable of accumulating at least 5% of free L-arginine on a dry cell weight basis after said mutation treatment, cultivating said desired yeast and recovering said desired yeast from the resulting culture.

3. A process for producing a yeast with a high arginine content according to claim 2, wherein the yeast Kluyveromyces is *Kluyveromyces polysporus*.

4. A process for producing yeast a with a high arginine content according to claim 3, wherein the yeast belonging to *Kluyveromyces polysporus* is *Kluyveromyces polysporus* ETA 82-33 (FERM BP-2560).

5. A process for producing a yeast with a high arginine content according to claim 2, wherein the mutation treatment is UV irradiation.

6. A process for producing a yeast with a high arginine content according to claim 2, wherein the mutation treatment is chemical treatment.

7. A process for producing a yeast with a high arginine content according to claim 6, wherein the chemical treatment is chemical treatment with N-methyl-N'-nitro-N-nitrosoguanidine.

* * * * *